United States Patent [19]

Matsui et al.

[11] Patent Number: 5,370,822
[45] Date of Patent: Dec. 6, 1994

[54] 2-FLUOROBENZONITRILE DERIVATIVE

[75] Inventors: Shuichi Matsui; Yuichi Onji; Atsuko Fujita; Tomoyuki Kondo; Yasuyuki Goto, all of Chiba, Japan

[73] Assignee: Chisso Corporation, Ohsaka, Japan

[21] Appl. No.: 118,668

[22] Filed: Sep. 10, 1993

[30] Foreign Application Priority Data

Sep. 11, 1992 [JP] Japan .................................. 4-243635

[51] Int. Cl.⁵ ..................... C09K 19/30; C07C 255/50
[52] U.S. Cl. ................... 252/299.63; 558/411; 558/425
[58] Field of Search .......... 252/299.01, 299.4, 299.61, 252/299.63; 558/411, 425

[56] References Cited

U.S. PATENT DOCUMENTS 5,055,220  8/1991  Uchida et al. .................. 252/299.01

FOREIGN PATENT DOCUMENTS 0470590  2/1992  European Pat. Off. .
3509170  9/1986  Germany .
4-210669  7/1992  Japan .

OTHER PUBLICATIONS

Patent Abstracts of Japan, vol. 016, No. 552 (C-1006), Nov. 20, 1992 & JP-A-04 210 669 (Dainippon Ink), Jul. 31, 1992.

*Primary Examiner*—Shean Wu
*Attorney, Agent, or Firm*—Wenderoth, Lind & Ponack

[57] ABSTRACT

A novel liquid crystal compound exhibiting a low driving voltage, a liquid crystal phase within a broad temperature range and a good compatibility with other known liquid crystal compounds at low temperatures is provided, which compound is expressed by the formula

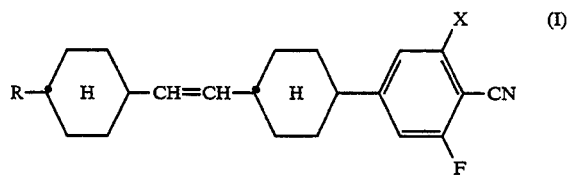

wherein R is H or a linear or branched alkyl group of 1-10C, X is H or F, and the vinyl group has a transconfiguration. This compound has a high dielectric anisotropy value for its relatively low viscosity and can drive liquid crystal display elements under a low voltage, and further exhibits a liquid crystal phase within a broad temperature range of about room temperature to about 200° C., and exhibits a good compatibility with many other liquid crystalline compounds such as ester compounds, Schiff's base compounds, biphenyls, phenylcyclohexanes, heterocyclic compounds, fluorine compounds, etc., particularly a good compatibility at low temperatures, and hence can provide improved liquid crystal materials. Further, when the compound of the present invention is added as a component of liquid crystal materials, it is possible to notably broaden the use temperature range of liquid crystal compositions without raising the viscosity.

4 Claims, No Drawings

2-FLUOROBENZONITRILE DERIVATIVE

BACKGROUND OF THE INVENTION

1. Field of the Invention

This invention relates to a 2-fluorobenzonitrile derivative. More particularly, it relates to a 4-[trans-4-[(E)-2-(trans-4-alkylcyclohexyl)vinyl]cyclohexyl]-2-fluorobenzonitrile and a liquid crystal composition containing the above compound as an effective component.

2. Description of the Related Art

Liquid crystal display elements utilize the optical anisotropy and the dielectric anisotropy of liquid crystal substances, and as the display mode of the elements, TN mode (twisted nematic mode), supertwisted nematic mode (STN mode), dynamic scattering mode (DS mode), guest-host mode (G-H mode), DAP mode, etc. are known. Further, as the method for driving these modes, static driving method, multiplex driving method, active matrix driving method, two-frequency driving method, etc. have been employed. The properties of liquid crystal substances used for these liquid crystal display elements are various, but any liquid crystal substances are common in the aspect of stability to moisture, air, heat, light, etc. Further, it is required for the elements that the liquid crystal phases are exhibited within a temperature range as broad as possible, around room temperature; the viscosity is low; and in the display element, a quick response rate, a high contrast and further a low driving voltage are required- Further, it is necessary that an adequate dielectric anisotropy ($\Delta\epsilon$) is effected depending upon the kind of display element. However, a single liquid crystal compound satisfying these characteristics has not yet been known. Thus, it is the present status that liquid crystal compositions obtained by blending several kinds of liquid crystal compounds and non-liquid crystalline compounds have been used.

Now, the following compounds similar to those of the present invention have been disclosed:

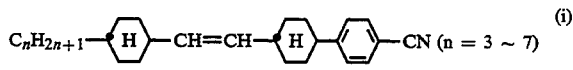

(Japanese patent application laid-open No. Sho 61-215336)

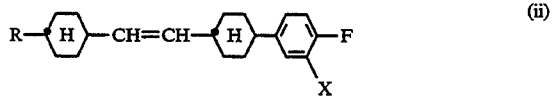

(U.S. Pat. No. 5,055,220)

wherein R represents an alkyl group of 1 to 8 carbon atoms and X represents a hydrogen atom or a fluorine atom.

With regard to the compound (i), no example is disclosed in the above Japanese patent application laid-open No. Sho 61-215336, and according to the study of the present inventors, the compound has drawbacks that it has a high viscosity for its dielectric anisotropy value and an inferior compatibility with other liquid crystalline compounds. Further, the compound (ii), too, has drawbacks that it has a small dielectric anisotropy value ($\Delta\epsilon$) and its temperature range wherein the liquid crystal phase is exhibited is narrow.

Thus, the present inventors have made extensive research in introduction of 2-fluorobenzonitrile derivative into the core structure of an alkyldicyclohexylethylene, and as a result, have invented a novel liquid crystalline substance described below, which exhibits a low viscosity and a nematic phase within a notably broad temperature range, has a high dielectric anisotropy value and a good compatibility with other liquid crystalline compounds at low temperatures.

The object of the present invention is to provide a novel liquid crystal compound having a large dielectric anisotropy value, exhibiting liquid crystal phases within a broad temperature range and having a good compatibility with other known liquid crystal compounds at low temperatures, and a liquid crystal composition containing the same.

SUMMARY OF THE INVENTION

The present invention resides in a 2-fluorobenzonitrile derivative expressed by the formula

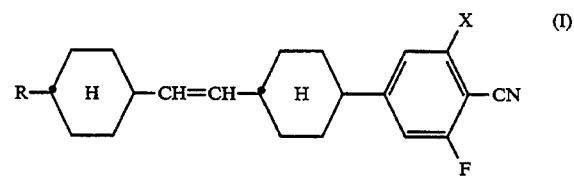

wherein R represents a hydrogen atom or a linear or branched alkyl group of 1 to 10 carbon atoms, X represents a hydrogen atom or a fluorine atom, and the vinyl group has a trans-configuration, and a liquid crystal composition containing said derivative as an effective component.

The liquid crystal composition provided by the present invention is a liquid crystal dielectric comprising a component (A) containing at least one compound expressed by the formula (I), and at least one member selected from the group consisting of a component (B) containing at least one compound of a high dielectric anisotropy of preferably $\Delta\epsilon \geq 5$, a component (C) containing at least one compound of a low dielectric anisotropy of preferably $|\Delta\epsilon| < 5$, a component (D) containing at least one compound having a clearing point exceeding 80° C. and another component (E).

DETAILED DESCRIPTION OF PREFERRED EMBODIMENTS

Particularly preferable compounds as the component (B) of the present invention are illustrated below.

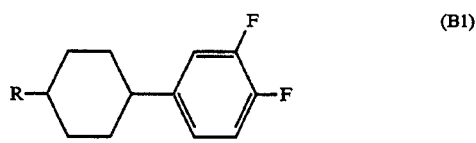

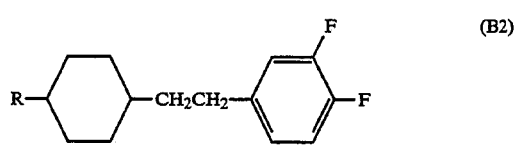

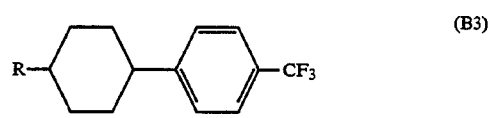

-continued
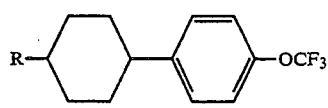 (B4)
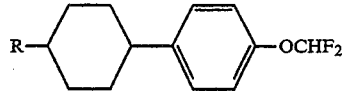 (B5)
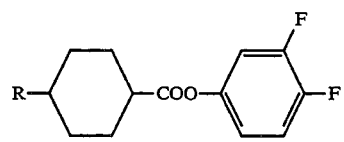 (B6)
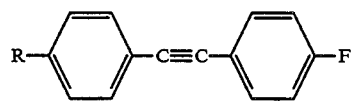 (B7)
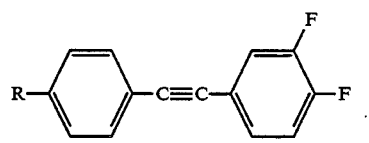 (B8)
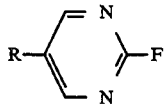 (B9)
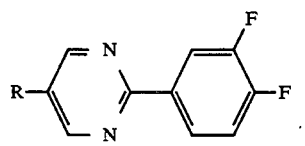 (B10)
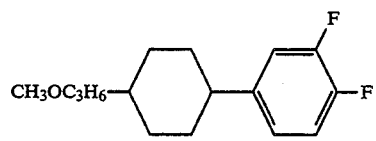 (B11)
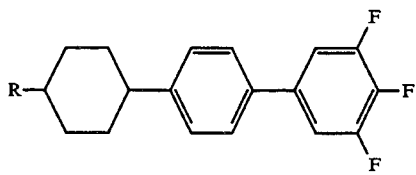 (B12)
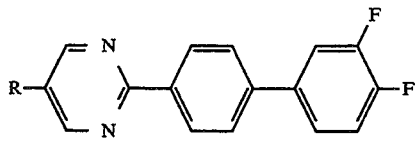 (B13)
In the above compounds, R represents an alkyl group or an alkenyl group of 1 to 10 carbon atoms, one or two non-adjacent carbon atoms of which may be substituted by oxygen atom(s).
Particularly preferable compounds as the component (C) illustrated below.
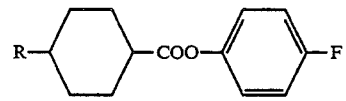 (C1)
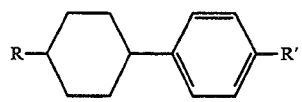 (C2)
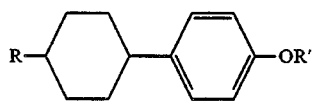 (C3)
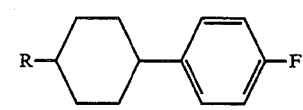 (C4)
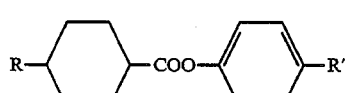 (C5)
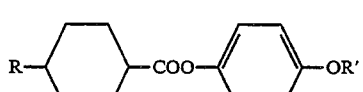 (C6)
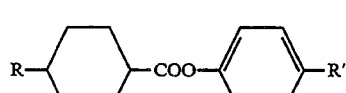 (C7)
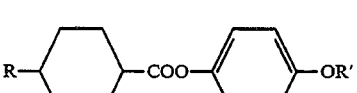 (C8)
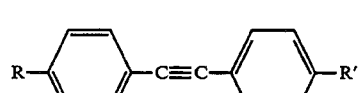 (C9)
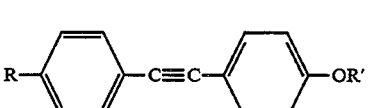 (C10)
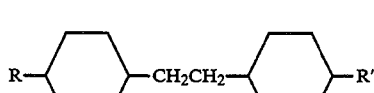 (C11)
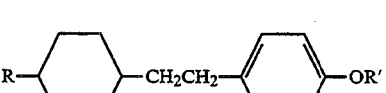 (C12)
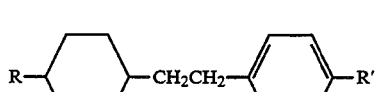 (C13)
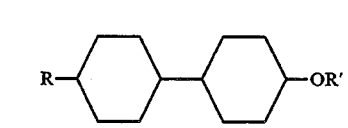 (C14)

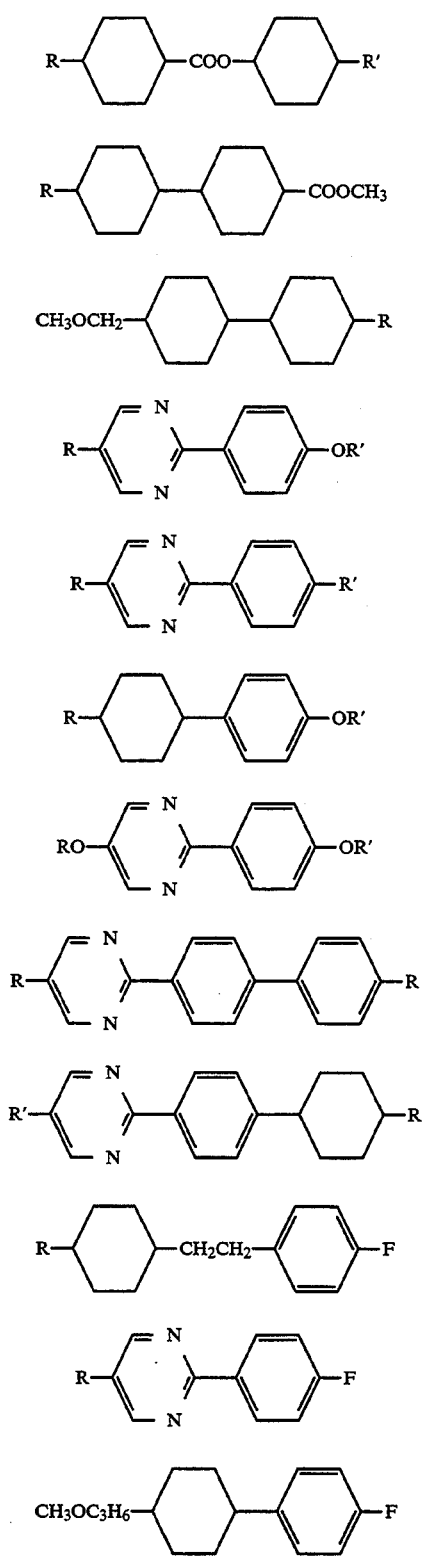
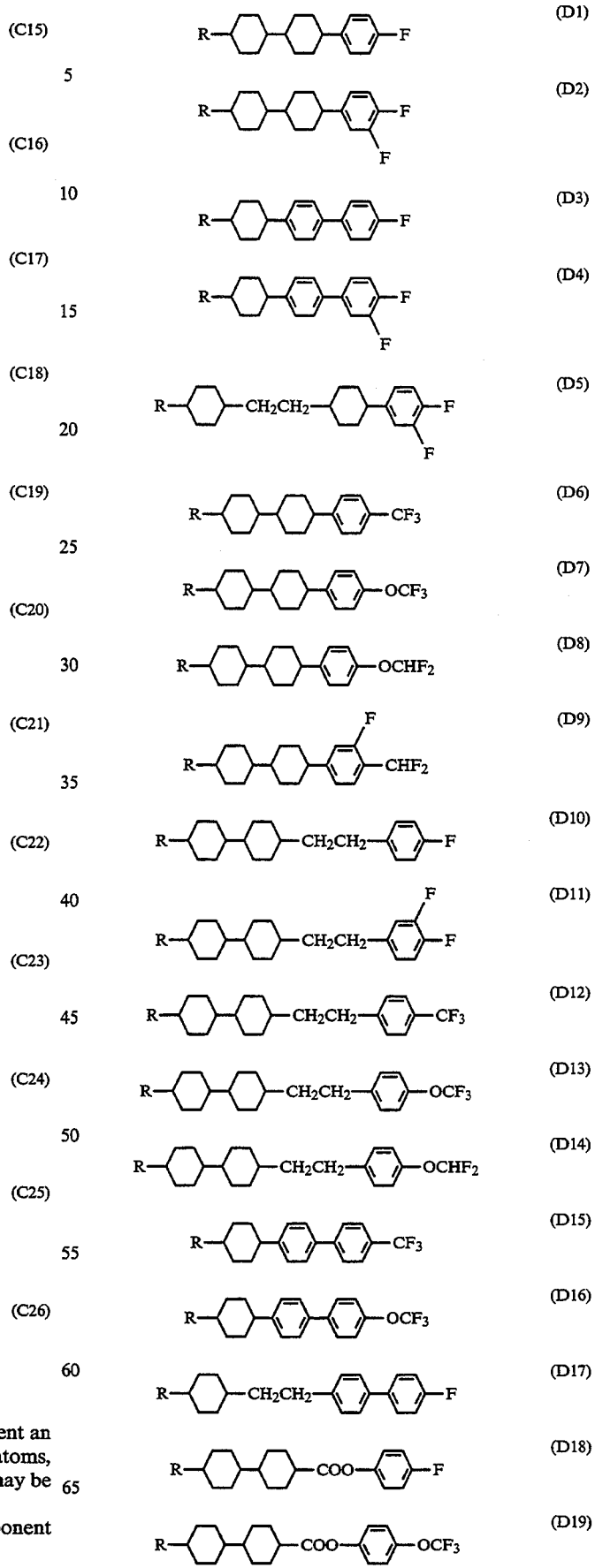
In the above compounds, R and R' each represent an alkyl group or an alkenyl group of 1 to 10 carbon atoms, one or two non-adjacent carbon atoms of which may be substituted by oxygen atom(s).
Particularly preferable compounds as the component (D) are illustrated below.

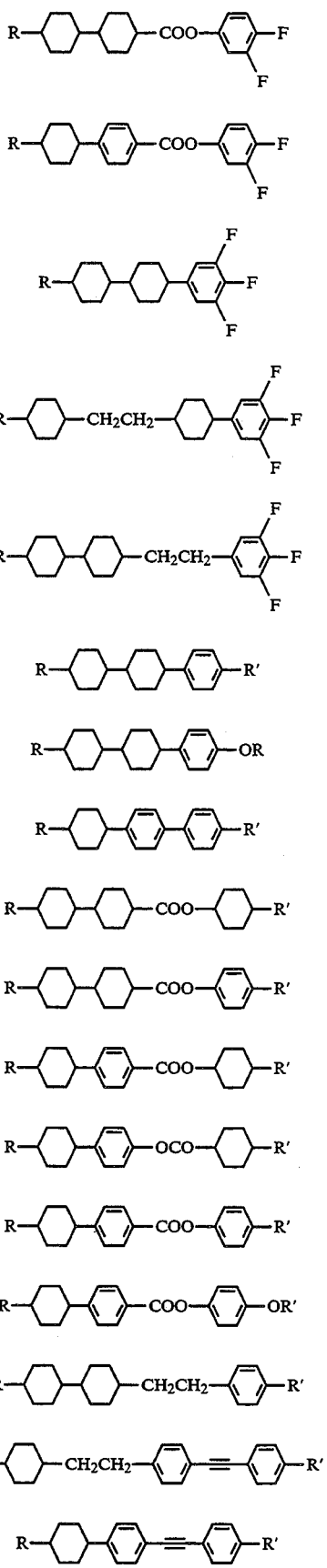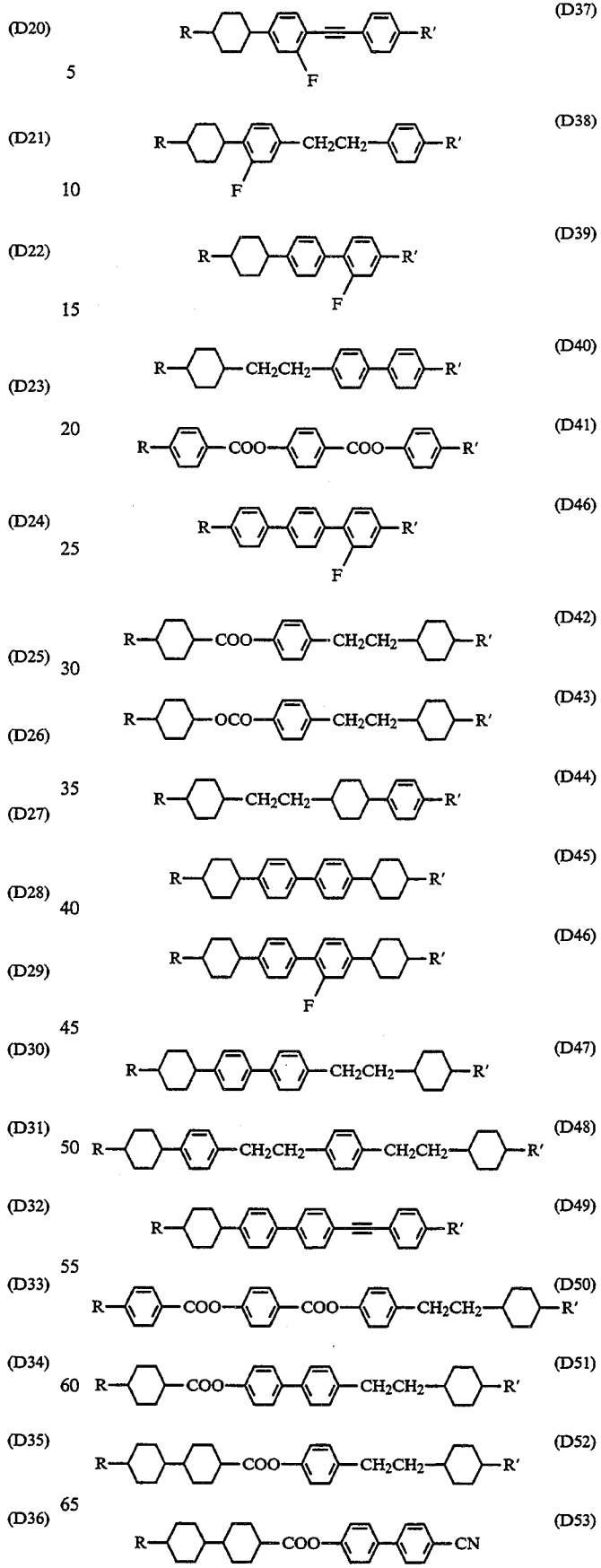

-continued
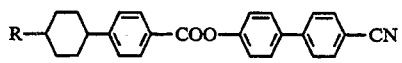 (D54)
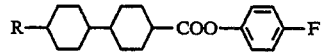 (D55)
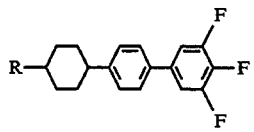 (D56)
In the above compounds, R and R' each represent an alkyl group or an alkenyl group of 1 to 10 carbon atoms, one or two non-adjacent carbon atoms of which may be substituted by oxygen atom(s).
Particularly preferable compounds as the component (E) are illustrated below.
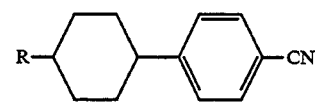 (E1)
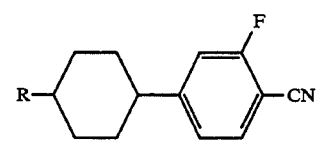 (E2)
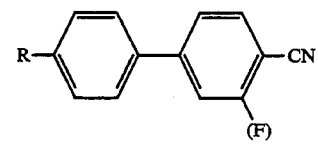 (E3)
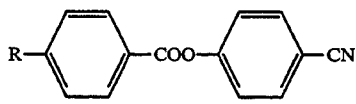 (E4)
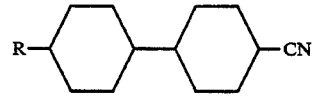 (E5)
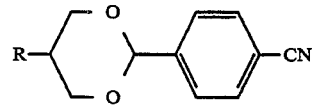 (E6)
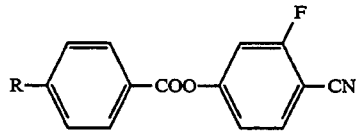 (E7)
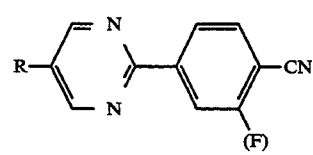 (E8)
-continued
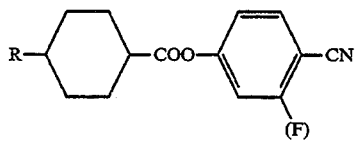 (E9)
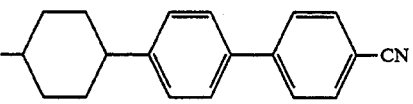 (E10)
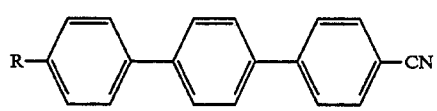 (E11)
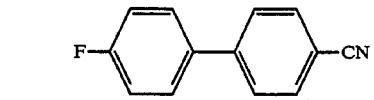 (E12)
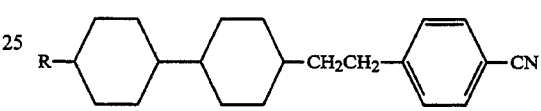 (E13)
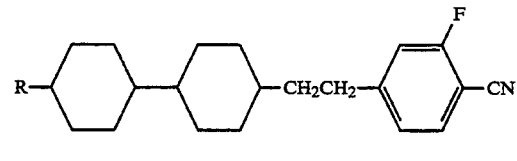 (E14)
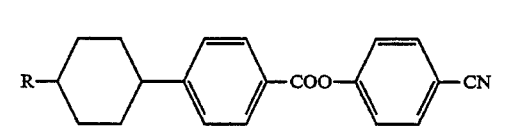 (E15)
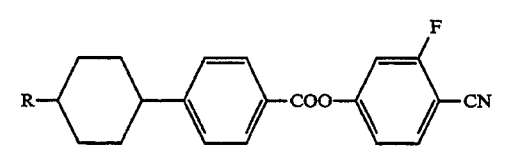 (E16)
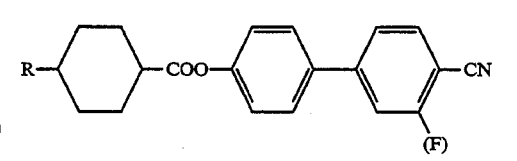 (E17)
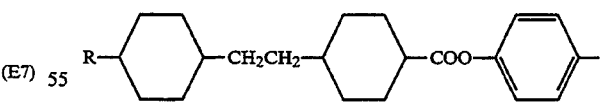 (E18)
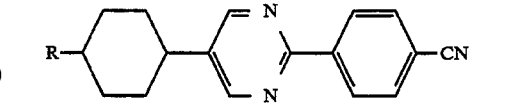 (E19)
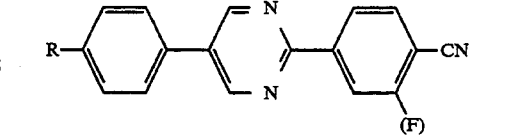 (E20)

-continued

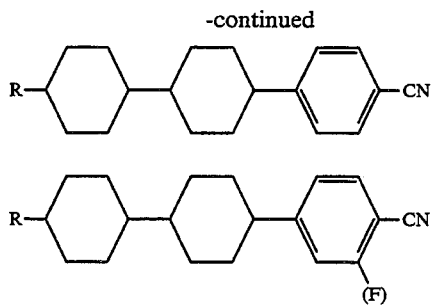

In the above compounds, R represents an alkyl group or an alkenyl group of 1 to 10 carbon atoms, one or two non-adjacent carbon atoms of which may be substituted by oxygen atom (s).

It is preferred for the composition of the present invention to contain at least one compound expressed by the formula (I) in a proportion of 0.1 to 40% by weight, in that the resulting liquid crystal characteristics are superior. Preferable compounds of the formula (I) of the present invention are expressed by the following formulas:

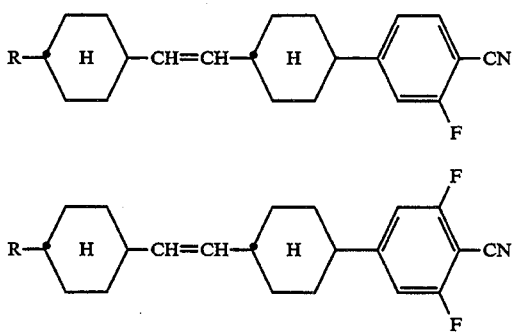

In these formulas, R represents a hydrogen atom or a linear or branched alkyl group of I to 10 carbon atoms and the vinyl group has a trans-configuration.

It is known that the core structure of dicyclohexylethylene in the molecule has an effect of broadening the temperature range of a nematic phase, but it has been found in the invention that when the structure is combined with a 2-fluorobenzonitrile derivative, the above effect is notably improved, and thus, the compounds (I-a) and (I-b) both exhibit a nematic liquid crystal phase within a broad range of about room temperature to about 200° C. Further, it has been found that both the compounds have a relatively low viscosity for a tricyclic compound, and nevertheless have a large positive dielectric anisotropy value (Δε). Particularly the compound (I-b) has a notably large dielectric anisotropy value and thereby makes it possible to drive liquid crystal display elements at a low voltage; hence it is optimum as a material for liquid crystal display elements.

The compound of the present invention is electrically stable, and also stable to heat, air, light, etc., exhibits a liquid crystal phase within a broad temperature range and has a large dielectric anisotropy value. Further, the compound of the present invention has a good compatibility with other liquid crystalline compounds and particularly a good compatibility at low temperatures; hence it can provide a liquid crystal material having improved specific properties.

PREPARATION OF THE COMPOUND

Next, the preparation process of the compound of the present-invention is described. The process is divided into a preparation of 1-formyl-4-(3-fluoro-4-cyanophenyl)cyclohexanone as a raw material and preparations of the respective compounds using the same.

The preparation of 1-formyl-4-(3-fluoro-4-cyanophenyl)cyclohexane is carried out as follows:

1,4-Cyclohexanedionemonoethyleneketal is reacted with a Grignard reagent prepared from 3-fluorobromobenzene (1), to obtain an alcohol form substance (2), followed by dehydrating it with an acid catalyst (such as p-toluenesulfonic acid, potassium hydrogen sulfate, hydrochloric acid, sulfuric acid, ion-exchange resin, etc.) to convert it into a cyclohexene derivative (3), thereafter subjecting the derivative to catalytic hydrogenation reaction in the presence of a catalyst such as Pd, Ni, Pt, etc., further deprotecting with an acidic aqueous solution (such as acetic acid, hydrochloric acid, formic acid, etc.), to obtain a cyclohexanone derivative (5), next reacting oxalyl chloride for acylation with the compound (5) in the presence of aluminum chloride, to obtain an acid chloride derivative (6), reacting aqueous ammonium with (6) to obtain an amide form substance (7), further reacting benzenesulfonyl chloride with (7) in pyridine, to obtain 4-(3-fluoro-4-cyanophenyl)cyclohexanone (8), reacting an ylide obtained by treating methoxymethylphosphonium chloride with a base (such as n-butyllithium, potassium-t-butoxide, etc.), with the cyclohexanone derivative (8) and further treating it in an acidic aqueous solution to obtain the objective 1-formyl-4-(3-fluoro-4-cyanophenyl) cyclohexane. 1-Formyl-4-(3,5-difluoro-4-cyanophenyl) cyclohexane, too, can be prepared in the same manner as the above, using 3,5-difluorobromobenzene as its raw material.

Using the thus obtained 1-formyl-4-(3-fluoro-4-cyanophenyl)cyclohexane, the objective 4-[trans-4-[(E)-2-(trans-4-alkylcyclohexyl)vinyl]cyclohexyl]-2-fluorobenzonitrile derivative can be prepared according to the following preparation.

A base (such as n-butyllithium, potassium-t-butoxide, etc.) is reacted with a quaternary salt (9) derived from an alkylcyclohexylmethyl bromide and triphenylphosphine to form an ylide, followed by reacting an aldehyde derivative (8) with the ylide, to obtain a dicyclohexylethylene derivative (10) which is a mixture of E-form and Z-form, the ratio (Z/E) being 95/5, and converting the Z-form into E-form, to obtain the compound of the present invention (I-a). Namely, E mixture is oxidized with a peroxide such as m-chloroperbenzoic acid, etc. in dichloromethane, to obtain an oxirane derivative (11), followed by brominating it with dibromotriphenylphosphorane to obtain a bromo form substance (12) which is a mixture of erythro-form and threo-form, recrystallizing it from a suitable solvent, to separate only the erythro-form, and reducing it with zinc powder, to obtain a 4-[trans-4-[(E)-2-(trans-4-alkylcyclohexyl)vinyl]cyclohexyl]-2-fluorobenzonitrile derivative which is the compound of the present invention. Further, a 4-[trans-4-[(E)-2-(trans-4-alkylcyclohexyl)vinyl]-cyclohexyl]-2,6-difluorobenzonitrile derivative which is a compound of the present invention, too, can be prepared according to the same preparation, using 1-formyl-4-(3,5-difluoro-4-cyanophenyl)cyclohexane as its raw material.

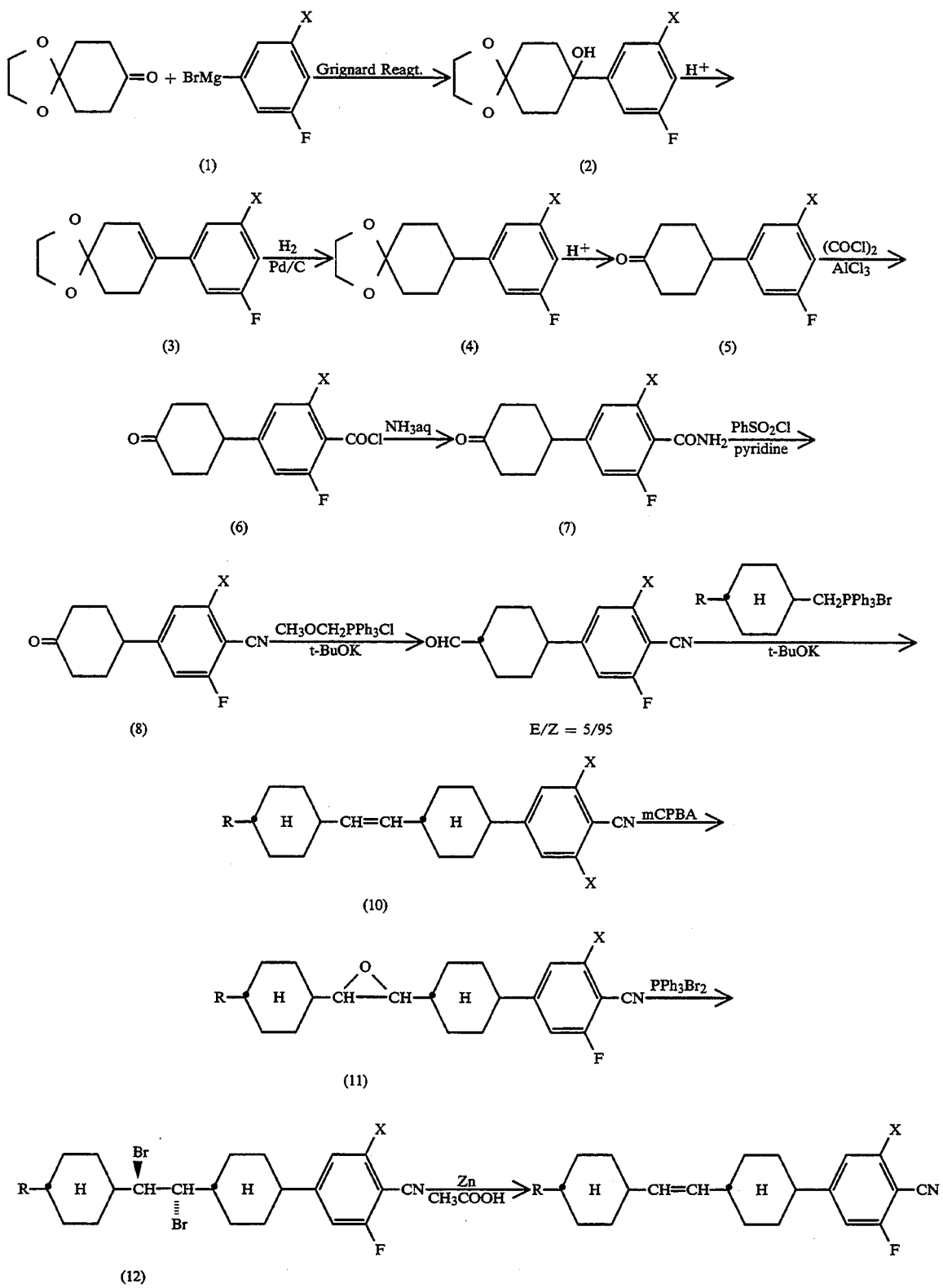

In the above formulas, R represents a hydrogen atom or a linear or branched alkyl group of 1 to 10 carbon atoms and X represents a hydrogen atom or a fluorine atom.

The compound of the present invention exhibits a high dielectric anisotropy for its relatively low viscosity and can drive liquid crystal display elements under a low voltage. Further, a compound (ii) disclosed in the above U.S. Pat. No. 5,055,220 (R=n—$C_3H_7$ and X=F) exhibits a nematic phase-isotropic liquid phase transition point of 39.0° to 131.8° C., whereas a compound of the present invention (R=n—$C_3H_7$ and X=H, in the formula (I)) exhibits its liquid crystal phase within a temperature range as notably broad as 48.0° to 215.5° C. Further, the compound of the present invention has a good compatibility with many other liquid crystalline compounds such as those of ester compounds, Schiff's base compounds, biphenyl compounds, phenylcyclohexane compounds, heterocyclic compounds, fluorine compounds, etc., particularly a good compatibility at low temperatures; thus, it is possible to provide an improved liquid crystal material. Further, by adding the compounds of the present invention as components of a liquid crystal composition, it is possible to notably broaden the temperature range in which the liquid crystal composition is used, without raising the viscosity.

EXAMPLE

The preparation of the compound of the present invention and its use example will be described in more detail by way of Examples, but it should not be construed to be limited thereto.

In addition, the symbols in the respective Examples are as follows:

CN point: crystal-nematic phase transition point
NI point: nematic phase-isotropic liquid phase transition point

EXAMPLE 1

Preparation of 1-formyl-4-(3-fluoro-4-cyanophenyl)-cyclohexane

1) Flaked magnesium (20.5 g, 0.844 mol) and tetrahydrofuran (hereinafter abbreviated to THF) (10 ml) were added into a three-neck flask provided with a thermometer, a stirrer, a cooling tube and a dropping funnel, followed by dropwise adding a THF solution (250 ml) of 3-fluorobromobenzene (134.5 g, 0.77 mol) with stirring for one hour so that the temperature inside the system might be kept at 50° C., thereafter aging the mixture at the same temperature for 2 hours in a hot bath to prepare 3-fluorophenylmagnesium bromide. Thereafter a THF solution (200 ml) of cyclohexanedionemonoethylene ketal (100 g, 0.64 mol) was dropwise added into the above prepared Grignard reagent for one hour so that the temperature inside the system might be kept at 50° C., followed by aging the mixture with stirring for 3 hours while keeping the same temperature at 50° C. in the hot bath, thereafter adding a saturated aqueous solution (200 ml) of anunonium chloride into the reaction solution, filtering off insolubles with Celite, extracting with toluene (1,000 ml), washing the extract layer with water (1,500 ml), drying it over anhydrous magnesium sulfate, and distilling off toluene, to obtain brown crystals (165.1 g), which are those of an alcohol derivative. This alcohol derivative was used in the subsequent step, as it was.

2) The alcohol derivative (165.1 g) obtained in the above step 1) was dissolved in toluene (900 ml) in a 2 l capacity three-neck flask provided with a stirrer, a thermometer and a Dean-Stark device, followed by adding an ion exchange resin, Amberlite (8.3 g) as an acid catalyst, heating the mixture under reflux with stirring for one hour, allowing the reaction solution to cool down to room temperature, filtering off the catalyst, drying over anhydrous magnesium sulfate, distilling off toluene under reduced pressure, to obtain a yellow-brown oily substance (165.1 g) which was a cyclohexene derivative. This cyclohexene derivative was purified by distillation under reduced pressure, to obtain a fraction of 158°-163° C./3 mmHg (112.5 g), which was then subjected to catalytic hydrogenation. Namely, the cyclohexene derivative (112.5 g) was dissolved in Solmix (500 mE) in a 1 l capacity eggplant flask, follwed by adding 5%-Pd/C catalyst (10 g) and subjecting the mixture to catalytic hydrogenation at room temperature under a hydrogen pressure of 5 to 10 Kg/cm² for 5 hours. After completion of the reaction, the catalyst was separated off, followed by distilling off the solvent under reduced pressure, concentrating the residue to obtain an indigo colored oily substance (111.1 g). The reaction substance thus obtained was used for deprotection, as it was. Namely, the reduced and purified substance (111.1 g) was dissolved in toluene (150 ml) in a 1 l eggplant flask, followed by adding 98% formic acid (132.4 g, 2.82 mols), heating the mixture under reflux for 4 hours, allowing the resulting reaction solution to cool down to room temperature, pouring it into ice-cooled water (500 ml), extracting with toluene (800 ml), washing the extract layer with water (400 ml), washing it with a saturated aqueous solution of sodium carbonate (300 ml) and with water (900 ml) in this order, drying over anhydrous magnesium sulfate, to obtain a brown oily substance (102.3 g). The reaction mixture was subjected to distillation under reduced pressure to separate a fraction of 145°-148° C./4 mmHg which was 4-(3-fluorophenyl)cyclohexanone (colorless oily substance)(82.1 g).

3) Aluminum chloride (106.8 g, 0.80 mol) and dichloromethane (600 ml) were added into a three-neck flask provided with a stirrer, a thermometer, a cooling tube, a nitrogen gas-introducing tube and a dropping funnel, followed by cooling the mixture down to −5° C. with salt-ice, adding 4-(3-fluorophenyl)cyclohexanone (51.3 g, 0.27 mol) with stirring, dropwise adding oxalyl chloride (94.8 g, 0.75 mol) in nitrogen gas atmosphere for 2 hours while keeping the temperature at −5° to −2° C., thereafter raising the reaction temperature up to 10° C., stirring for 4 hours while keeping the temperature at 10° C., thereafter gradually dropwise adding the reaction solution into ice water (2,000 ml) to decompose unreacted oxalyl chloride, separating dichloromethane layer, further extracting the aqueous layer with dichloromethane (500 ml), mixing the extract layers, washing with water (1,000 ml), drying over anhydrous magnesium sulfate, and distilling off the solvent under reduced pressure to obtain a brown oily substance (62.9 g). The thus obtained acid chloride derivative was suspended in dioxane (100 ml), followed by cooling the suspension down to 0° C. with ice, gradually dropwise adding 25% aqueous ammonia (100 ml), for 20 minutes so as not to exceed 10° C., thereafter stirring the mixture for 2 hours at 10° C., filtering off an amide substance deposited from the reaction solution, followed by washing with water (500 ml) and drying under reduced pressure, to obtain brown crystals (39.1 g).

4) The amide substance thus obtained (39.1 g) was dissolved in pyridine (200 ml) and toluene (300 ml) in a 1 l capacity eggplant type flask provided with a stirrer and a cooling tube, followed by adding benzenesulfonyl chloride (43.9 g, 0.25 mol), heating the mixture under reflux for 2 hours, cooling the reaction solution down to room temperature, adding water (300 ml), separating a toluene layer, further extracting the aqueous layer with toluene (400 ml), mixing the extract layers, washing with 6N-HCl aqueous solution (200 ml), water (400 ml), a saturated aqueous solution of sodium carbonate (300 ml) and water (800 ml), in this order, drying over anhydrous magnesium sulfate, distilling off toluene under reduced pressure, to obtain yellow-brown crystals (32.3 g). The reaction mixture was purified according to silica gel column chromatography using a mixed solvent of toluene/ethyl acetate as a developing solvent, to obtain 4-(3-fluoro-4-cyanophenyl)cyclohexanone (pale yellow crystals) (30.8 g).

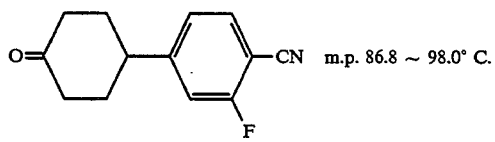 m.p. 86.8 ~ 98.0° C.

5) Methoxymethyltriphenylphosphine chloride (61.9 g, 0.8 mol) was suspended in THF (250 ml) in nitrogen gas atmosphere in a three-neck flask provided with a stirrer, a thermometer and a nitrogen gas-introducing tube, followed by cooling the suspension down to 0° C. with ice with stirring, adding potassium t-butoxide (21.5 g, 0.19 mol), gradually elevating the temperature up to room temperature (20° C.) for 3 hours with stirirng, again cooling down to 0° C. with ice, dropwise adding a THF solution (50 ml) of 4-(3-fluoro-4-cyanophenyl)cyclohexanone (24.5 g, 0.11 mol) for 20 minutes so as to keep the temperature at 0° C., gradually raising the temperature up to room temperature for 20 hours with stirring, adding water (300 ml) to complete the reaction, separating the THF layer from the reaction solution, further extracting the aqueous layer with ethyl acetate (300 ml), mixing the extract layers, washing with water (900 ml), drying over anhydrous magnesium sulfate, distilling off the solvent under reduced pressure, to obtain the reaction mixture. The reaction mixture was purified according to silica gel chromatography using toluene as a developing solvent, to obtain a colorless, oily substance (22.3 g). This reaction substance was dissolved in THF (600 ml) in nitrogen atmosphere, followed by adding 2N-HCl aqueous solution (165 ml), agitating at room temperature for 20 hours, and extracting the reaction solution with ethyl acetate (500 ml). The extract layer was washed with water (300 ml), a saturated aqueous solution of sodium carbonate (300 ml) and water (900 ml), in this order, followed by drying over anhydrous magnesium sulfate and distilling off the solvent under reduced pressure, to obtain the objective 1-formyl-4-(3-fluoro-4-cyanophenyl)cyclohexane (colorless, oily substance) (17.3 g).

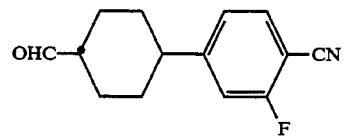

EXAMPLE 2

Preparation of 1-formyl-4-(3,5-difluoro-4-cyanophenyl)cyclohexane

1) Flaked magnesium (13.9 g, 0.57 mol) and tetrahydrofuran (10 ml) were added into a three-neck flask provided with a thermometer, a stirrer, a cooling tube and a dropping funnel, followed by dropwise adding a THF solution (150 ml) of 3,5-difluoro-bromobenzene (100.0 g, 0.52 mol) with stirring for one hour so as to keep the inside temperature at 50° C., thereafter aging the mixture at the same temperature for 2 hours in a hot bath, to prepare 3,5-difluorophenylmagnesium bromide. Next, a THF solution (100 ml) of cyclohexanedionemonoethyleneketal (62.3 g, 0.40 mol) was dropwise added into the prepared Grignard reagent for one hour so as to keep the temperature inside the reaction system at 50° C., followed by stirring for 3 hours while keeping the temperature inside the hot bath at the same temperature, thereafter adding a saturated aqueous solution of ammonium chloride (200 ml) to the reaction solution, filtering off insolubles, extracting with toluene (1,000 ml), washing the extract layer with water (1,500 ml), drying over anhydrous magnesium sulfate, and distilling off toluene under reduced pressure, to obtain brown crystals (110.8 g). This is an alcohol derivative. The alcohol derivative was used at the succeeding step, as it was.

2) The alcohol derivative (110.8 g) obtained at the step 1) was added and dissolved in toluene (600 cc) in a 2 l capacity three-neck flask provided with a stirrer, a thermometer and a Dean-Stark's device, followed by adding an ion-exchange resin, Amberlite (5.5 g) as an acid catalyst, heating the mixture under reflux with stirring for one hour, allowing the reaction solution to cool down to room temperature, filtering off the catalyst, drying over anhydrous magnesium sulfate, distilling off toluene under reduced pressure, to obtain a cyclohexene derivative (a yellow-brown oily substance) (105.1 g). This substance was subjected to distillation under reduced pressure for purification, to obtain a fraction of 111.0°-129.0° C./1-5 mmHg (76.4 g). This cyclohexene derivative was then subjected to catalytic hydrogenation. Namely, the cyclohexene derivative (76.4 g) was dissolved in Solmix (500 ml) in a 1 l capacity eggplant type flask, followed by adding 5%-Pd/C catalyst (7.0 g), subjecting the derivative to catalytic hydrogenation at room temperature under a hydrogen pressure of 5 to 10 Kg/cm$^2$ for 5 hours, thereafter filtering off the catalyst and distilling off the solvent under reduced pressure to obtain an indigo colored oily substance (76.6 g). The thus obtained reaction substance was used for deprotection, as it was. Namely, the redused and purified substance (76.6 g) was dissolved in toluene (100 ml) in a 1 l capacity eggplant type flask, followed by adding 98% formic acid (94.0 g, 2.04 mol), heating the mixture under reflux for 4 hours, allowing the mixture to cool down to room temperature, pouring the reaction solution into ice water (500 ml), extracting it with toluene (800 ml), washing the extract layer with water (400 ml), a saturated aqueous solution of sodium carbonate (300 ml) and water (900 ml), in this order, drying over anhydrous magnesium sulfate, to obtain brown crystals (69.8 g), which were recrsytallized from a mixed solvent of heptane/ethyl acetate, to obtsin 4-(3,5-difluorophenyl)cyclohexanone (colorless crystals) (53.3 g).

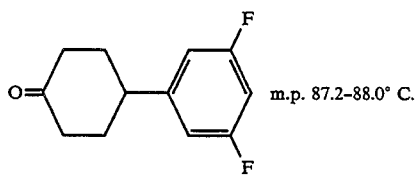

m.p. 87.2-88.0° C.

3) Aluminum chloride (110.08 g, 0.83 mol) and dichloromethane (600 ml) were added into a three-neck flask provided with a stirrer, a thermometer, a cooling tube, a nitrogen gas-introducing tube and a dropping funnel, followed by cooling the mixture with salt-ice down to −5° C., dropwise adding 4-(3,5-difluorophenyl)cyclohexanone (53.3 g, 0.25 tool), dropwise adding oxalyl chloride (95.2 g, 0.75 mol) in a nitrogen atmosphere with stirring for 2 hours while keeping the temperature at −5° to −2° C., thereafter raising the reaction temperature up to 10° C., stirring for 4 hours while keeping the temperature at 10° C., thereafter gradually dropwise adding the reaction solution into ice water (2,000 ml) to decompose unreacted oxalyl chloride, separating the dichloromethane layer, further extracting the aqueous layer with dichloromethane (500 ml), mixing the extract layers, washing with water (1,000 ml), drying over anhydrous magnesium sulfate, and distilling off the solvent under reduced pressure, to obtain an acid chloride derivative (brown, oily substance) (67.2 g). The acid chloride derivative was suspended in dioxane (100 ml), as it was, followed by cooling with ice down to 0° C., gradually dropwise adding 25% aqueous ammonia (100 ml) for 20 minutes so as not to exceed 10° C., thereafter agitating at 10° C. for 2 hours, filtering off the amide substance deposited from the reaction solution, washing with water (500 ml) and drying under reduced pressure, to obtain brown crystals (60.1 g). 4) The amide substance thus obtained (60.1 g) was dissolved in pyridine (300 ml) and toluene (300 ml) in a 1 l capacity eggplant type flask provided with a stirrer and a cooling tube, followed by adding benzenesulfonyl chloride (62.9 g, 0.36 mol), heating the mixture under reflux for 2 hours, cooling the reaction solution down to room temperature, adding water (300 ml), separating the toluene layer, extracting the aqueous layer with toluene (400 ml), mixing the extract layers, washing with 6N-HCl aqueous solution (200 ml), water (400 ml), a saturated aqueous solution of sodium carbonate (300 ml) and water (800 ml), in this order, drying over magnesium sulfate, and distilling off toluene under reduced pressure to obtain yellow-brown crystals (40.3 g). The reaction mixture was purified according to silica gel column chromatography using a mixed solvent of toluene/ethyl acetate as a developing solvent, to obtain 4-(3,5-difluoro-4-cyanophenyl)-cyclohexanone (pale yellow crystals) (33.4 g).

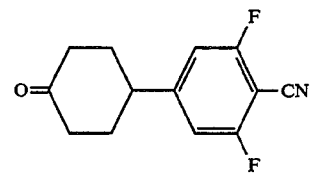

5) Methoxymethyltriphenylphosphine chloride (73.1 g, 0.21 mol) was suspended in THF (300 ml) in nitrogen gas atmosphere in a three-neck flask provided with a stirrer a thermometer and a nitrogen gas-introducing tube, followed by cooling the suspension with ice down to 0° C. with stirring, adding potassium t-butoxide (27.1 g, 0.24 mol), stirring for 3 hours while gradually raising the temperature up to room temperature (20° C.), again cooling with ice down to 0° C., dropwise adding a THF solution (60 ml) of 4-(3,5-difluoro-4-cyanophenyl)-cyclohexanone (33.4 g, 0.14 mol) for 20 minutes so as to keep the temperature at 0° C., stirring for 20 hours while gradually raising the temperature up to room temperature, adding water (300 ml) to complete the reaction, separating the THF layer from the reaction solution, extracting the aqueous layer with ethyl acetate (300 ml), mixing the extract layers, washing with water (900 ml), drying over anhydrous magnesium sulfate, and distilling off the solvent under reduced pressure, to obtain a reaction mixture. The reaction mixture was purified according to silica gel column chromatography using toluene as a developing solvent, to obtain a colorless, oily substance (34.5 g). The reaction substance was dissolved in THF (850 ml) in nitrogen gas atmosphere, followed by adding 2N-HCl aqueous solution (240 ml), stirring the mixture at room temperature for 20 hours, extracting the reaction solution with ethyl acetate (500 ml), washing the extract layer with water (300 ml), a saturated aqueous solution of sodium carbonate (300 ml) and water (900 ml), in this order, drying over anhydrous magnesium sulfate and distilling off the solvent under reduced pressure, to obtain the objective 1-formyl-4-(3,5-difluoro-4-cyanophenyl) cyclohexane (colorless, oily substance) (32.3 g).

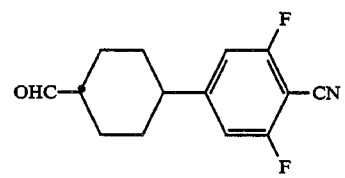

EXAMPLE 3

Preparation of 4-[trans-4-[(E)-2-(trans-4-ethylcyclohexyl)vinyl]cyclohexyl]-2-fluorobenzonitrile (a compound of the formula (I) wherein R=n-$C_2H_5$ and X=H)

1) Trans-4-ethylcyclohexylmethyl bromide (13.4 g, 65.1 mmol), triphenylphosphine (20.5 g, 78.1 mmols) and xylene (10 ml) were placed in a three-neck flask provided with a stirrer, a thermometer, a cooling tube and a nitrogen gas-introducing tube, followed by reacting them for 20 hours, while heating at 160° C. with stirring, allowing the reaction solution to cool down to room temperature, adding THF (250 ml) and potassium t-butoxide (6.8 g, 60.8 mmols) in this order, and stirring at room temperature for 3 hours, to prepare an ylide. Next, a THF solution (35 ml) of 1-formyl-4-(3-fluoro-4-cyanophenyl)cyclohexane (10 g, 43.4 mmols ) prepared in Example 1 was dropwise added into the ylide solution at room temperature for 20 minutes, followed by aging at room temperature for 20 hours with stirring, adding water (300 ml) to the reaction solution, to complete the reaction. The reaction solution was extracted with ethyl acetate (700 ml), followed by washing the extract layer with water (1,000 ml), drying over magnesium sulfate, and distilling off the solvent under reduced pressure, to obtain a reaction mixture, which was then purified according to silica gel column chromatography using toluene as a developing solvent, to obtain a brown-yellow substance (11.4 g). This product is 4-[trans-4-[(E,Z)-2-(trans-4-ethylcyclohexyl)vinyl]cyclohexyl]-2-fluorobenzonitrile. The ratio of E-substance to Z-substance formed is 5/95 (E-form/Z-form) according to the analytical results by way of gas chromatography.

2) m-Chloroperbenzoic acid (11.6 g, 67.2 mmols) and potassium carbonate (23.2 g, 167.9 mmols) were suspended in dichloromethane (200 ml) in a three-neck flask provided with a stirrer, a thermometer and a nitrogen gas-introducing tube, followed by cooling the mixture with ice with stirring, down to 0° C., dropwise adding a THF solution (50 ml) of 4-[trans-4-[(E,Z)-2-(trans-4-ethylcyclohexyl)-vinyl]cyclohexyl]-2-fluorobenzonitrile prepared at the step 1) (11.4 g, 33.6 mmols) for 30 minutes while keeping the temperature at 0° C., thereafter raising the temperature up to room temperature, stirring for 20 hours, as it was, pouring the reaction solution into a 10% aqueous solution of sodium thiosulfate, separating the dichloromethane layer, further extracting the aqueous layer with dichloromethane (200 ml), mixing the extract layers, washing with a saturated aquesous solution of sodium carbonate (600 ml) and water (600 ml) in this order, drying over anhydrous magnesium sulfate amd distilling off the solvent under reduced pressure for concentrating, to obtain an oxirane derivative (white crystals) (11.2 g).

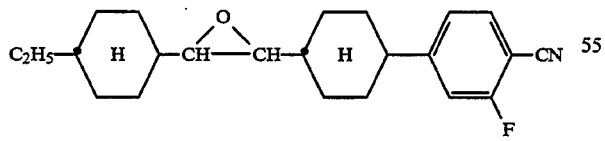

$^1$H—NMR (δppm); 2.4~2.8

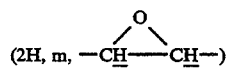
(2H, m, —CH——CH—)

3) The oxirane derivative (11.2 g, 31.0 mmols) obtained in the step 2), dibromotriphenylphosfolan (21.2 g, 50.1 mmols) and toluene (300 ml) were placed in an eggplant type flask provided with a stirrer, a thermometer and a cooling tube, followed by heating them under reflux for 9 hours, pouring the reaction solution into ice-cooled water, filtering off toluene-insolubles through Celite, newly adding toluene (300 ml) for extraction, washing the extract layer with water (600 ml), a saturated aqueous solution of sodium carbonate (300 ml) and water (600 ml) in this order, drying over anhydrous magnesium sulfate, distilling off the solvent under reduced pressure, to obtain a reaction mixture (25.3 g). The reaction mixture was purified according to silica gel column chromatography using toluene as a developing solvent and further recrystallizing only erythro-form substance from toluene, to obtain a dibromo derivative (colorless crystals) (2.53 g).

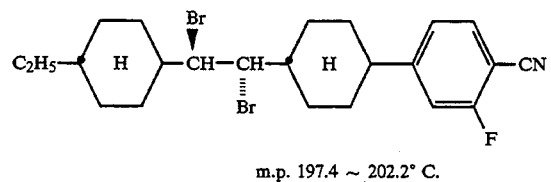

m.p. 197.4° ~ 202.2° C.

m.p. 197.4°~202.2° C.
$^1$H—NMR (δppm); 4.26 (2H, bs, —CHBrCHBr—)

4) The dibromo-form derivative (2.53 g, 2.5 mmols) prepared at the step 3) was suspended in acetic acid (30 ml) in nitrogen gas atmosphere in an eggplant type flask provided with a stirrer, followed by adding zinc powder (2.2 g, 32.9 mmols), stirring the mixture at room temperature for 17 hours, filtering off insolubles from the reaction solution, adding water (100 ml), extracting with ethyl acetate (200 ml), washing the extract layer with water (200 ml), a saturated aqueous solution of sodium carbonate (100 ml) and water (400 ml) in this order, drying over magnesium sulfate, and distilling off the solvent under reduced pressure, to obtain a reaction product (1.7 g). The reaction product was purified according to silica gel column chromatography using heptane as a developing solvent and recrystallizing from ethyl acetate, to obtain the finally object product, 4-[trans-4-[(E)-2-(trans-4-ethylcyclohexyl)vinyl]cyclohexyl]-2-fluorobenzonitrile (colorless crystals) (0.59 g).

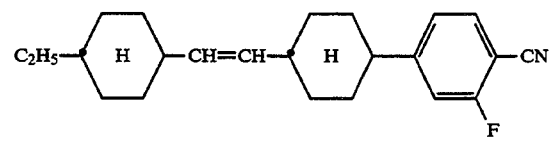

CN point 73.8°–74.3° C.
NI point 183.7°–188.5° C.
$^1$H—NMR (δppm); 5.3~5.4 (2H, m, —CH=CH—)

EXAMPLE 4

Preparation of 4-[trans-4-[(E)-2-(trans-4-propylcyclohexyl)vinyl]cyclohexyl]-2-fluorobenzonitrile (Compound of the formula (I) wherein R=n—C$_3$H$_7$ and X=H)

1) Trans-4-propylcyclohexylmethyl bromide (15.2 g, 69.5 mmols), triphenylphosphine (21.8 g, 83.4 mmols) and xylene (10 ml) were added into a three-neck flask provided with a stirrer, a thermometer, a cooling tube and a nitrogen gas-introducing tube, followed by reacting them for 20 hours, on heating at 160° C. with stirring, allowing the reaction solution to cool down to room temperature, adding THF (300 ml) and potassium t-butoxide (7.3 g, 65.1 mmols) in this order, stirring the mixture at room temperature for 3 hours to prepare an ylide. Next, a THF solution (35 ml) of 1-formyl-4-(3-fluoro-4-cyanophenyl)cyclohexane (10 g, 43.4 mmols) prepared in Example 1 is dropwise added into the solution of the above ylide at room temperature for 20 minutes, followed by aging at room temperature for 20 hours, adding water (300 ml) to the reaction solution, to complete the reaction. The reaction solution was extracted with ethyl acetate (700 ml), followed by washing the extract layer with water (1,000 ml), drying over magnesium sulfate, and distilling off the solvent under reduced pressure, to obtain a reaction mixture, which was then purified according to silica gel column chromatography using toluene as a developing solvent, to obtain a brown-yellow, oily substance (10.1 g) which was 4-[trans-4-[(E,Z)-2-(trans-4-propylcyclohexyl)-vinyl]cyclohexyl]-2-fluorobenzonitrile. The ratio of E-form to Z-form formed was E-form/Z-form=5/95, as a result of gas chromatography.

2) m-Chloroperbenzoic acid (9.8 g, 56.8 mmols) and potassium carbonate (19.6 g, 142.0 mmols) were suspended in dichloromethane (150 ml) in a three-neck flask provided with a stirrer, a thermometer and a nitrogen gas-introducing tube, followed by cooling the suspension with ice down to 0° C. with stirring, dropwise adding a THF solution (30 ml) of 4-[trans-4-[(E,Z)-2-(trans-4-propylcyclohexyl)-vinyl]cyclohexyl]-2-fluorobenzonitrile (10.1 g, 28.4 mmols) prepared at the step 1), for 40 minutes while keeping the temperature at 0 ° C., thereafter, raising the temperature up to room temperature, stirring for 20 minutes as it was, pouring the reaction solution into a 10% aqueous solution of sodium thiosulfate (300 ml), separating the dichloromethane layer, further extracting the aqueous solution with dichloromethane (200 ml), mixing the extract layers, washing with a saturated aqueous solution of sodium carbonate (600 ml) and water (600 ml) in this order, drying over magnesium sulfate and distilling off the solvent under reduced pressure, to obtain an oxirane derivative (white crystals) (8.33 g).

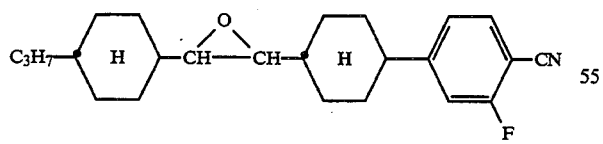

$^1$H—NMR (δppm); 2.4~2.8

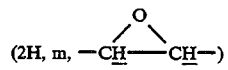

(2H, m, —CH——CH—)

3) The oxirane derivative (8.33 g. 16.2 mmols) obtained at the step 2), dibromotriphenylphosfolan (10.9 g, 25.9 mmols) and toluene (300 ml) were fed into an eggplant type flask provided with a stirrer, a thermometer and a cooling tube, followed by heating the mixture under reflux for 6 hours, pouring the reaction solution into ice-cooled water, filtering off toluene-insolubles through Celite, newly adding toluene (200 ml), extracting with toluene, washing the extract layer with water (600 ml), a saturated aqueous solution of sodium carbonate (300 ml) and water (600 ml), in this order, drying over magnesium sulfate, distilling off the solvent under reduced pressure, to obtain a reaction mixture (8.8 g). The reaction mixture was purified according to silica gel column chromatography using toluene as a developing solvent, followed by recrystallizing only erythro-form substance from toluene, to obtain a dibromo derivative (colorless crystals) (3.8 g).

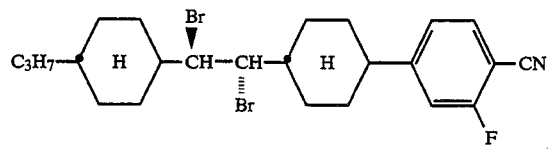

m.p. 180.7 ~ 182.8° C.

m.p. 180.7°~182.8° C.

$^1$H—NMR (δppm); 4.26 (2H, bs, —CHBrCHBr—)

4) The dibronto drivative (3.8 g, 7.4 mmols) prepared at the step 3) was suspended in acetic acid (40 ml) in nitrogen gas atmosphere in an eggplant type flask provided with a stirrer, followed by adding zinc powder (3.1 g, 47.8 retools), stirring the mixture at room temperature for 17 hours, filtering off insolubles from the reaction solution, extracting the reaction solution with ethyl acetate (200 ml), washing the extract layer with water (200 ml), a saturated aqueous solution of sodium carbonate (100 ml) and water (400 ml), in this order, drying over magnesium sulfate, and distilling off the solvent under reduced pressure, to obtain a reaction product (2.5 g). The reaction product was purified according to silica gel column chromatography using heptane as a developing solvent, followed by re-crystallizing from ethyl acetate, to obtain a finally objective substance, 4-[trans-4-[(E)-2-(trans-4-propylcyclohexyl)vinyl]cyclohexyl]-2-fluorobenzonitrile (colorless crystals) (1.2 g).

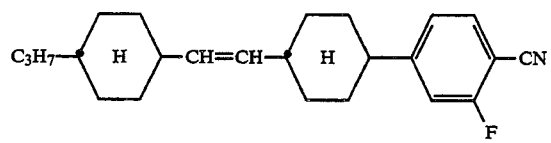

CN point 46.4°–48.0° C.
NI point 197.6°–215.5° C.
$^1$H—NMR (δppm); 5.3~5.4 (2H, m, —CH=CH—)

In the same manner as that of the above preparation, it is possible to prepare the following 4-[trans-4-[(E)-2-(trans-4-alkylcyclohexyl)vinyl]cyclohexyl]-2-fluorobenzonitriles, by replacing 4-propylcyclohexyl-methylbromide by 4-alkylcyclohexylmethylbromides having different alkyl groups:

4-[trans-4-[(E)-2-(trans-4-methylcyclohexyl)vinyl]cyclohexyl]-2-fluorobenzonitrile 4-[trans-4-[(E)-2-(trans-4-butylcyclohexyl)vinyl]cyclohexyl]-2-fluorobenzonitrile 4-[trans-4-[(E)-2-(trans-4-pentylcyclohexyl)vinyl]cyclohexyl]-2-fluorobenzonitrile CN point 48.5°–49.2° C.

NI point 176.2°–181.8° C.

4-[trans-4-[(E)-2-(trans-4-hexylcyclohexyl)vinyl]cyclohexyl]-2-fluorobenzonitrile 4-[trans-4-[(E)-2-(trans-4-heptylcyclohexyl)vinyl]cyclohexyl]-2-fluorobenzonitrile 4-[trans-4-[(E)-2-(trans-4-octylcyclohexyl)vinyl]cyclohexyl]-2-fluorobenzonitrile 4-[trans-4-[(E)-2-(trans-4-nonylcyclohexyl)vinyl]cyclohexyl]-2-fluorobenzonitrile 4-[trans-4-[(E)-2-(trans-4-decylcyclohexyl)vinyl]cyclohexyl]-2-fluorobenzonitrile

EXAMPLE 5

Preparation of 4-[trans-4-[(E)-2-(trans-4-propylcyclohexyl)vinyl]cyclohexyl]-2,6-difluorobenzonitrile (a compound of the formula (I) wherein R=n−$C_3H_7$ and X=F)

Trans-4-propylcyclohexylmethylbromide (15.2 g, 69.5 mmols), triphenylphosphine (21.8 g, 83.4 mmols) and xylene (10 ml) were fed into a three neck flask provided with a stirrer, a thermometer, a cooling tube and a nitrogen gas-introducing tube, followed by reacting them on heating at 160 ° C. with stirring, for 20 hours, allowing the reaction solution to cool down to room temperature, adding THF (300 ml) and potassium t-butoxide (7.3 g, 65.1 mmols) in this order, stirring the mixture at room temperature for 3 hours, as it was, to prepare an ylide. A THF solution (35 ml) of 1-formyl-4-(3,5-difluoro-4-cyanophenyl) cyclohexane (11.2 g, 45.0 mmols) prepared in Example 2, was dropwise added into the ylide solution, at room temperature for 20 minutes, followed by aging the mixture at room temperature for 20 hours with stirring, adding water (300 ml) to the reaction solution, to complete the reaction, extracting the reaction solution with ethyl acetate (700 ml), washing the extract layer with water (1,000 ml), drying over magnesium sulfate, and distilling off the solvent under reduced pressure, to obtain a reaction mixture. The resulting reaction substance was purified according to silica gel column chromatography using toluene as a developing solvent, to obtain a brown-yellow, oily substance (11.5 g). This substance is 4-[trans-4-[(E,Z)-2-(trans-4-propylcyclohexyl)vinyl]cyclohexyl]-2,6-difluorobenzonitrile. The proportion of E-form substance to Z-form substance is 5/95 as a result of analysis according to gas chromatography.

2) m-Chloroperbenzoic acid (10.7 g, 61.9 mmols) and potassium carbonate (21.4 g, 154.8 mmols) were suspended in dichloromethane (150 ml) in a three-neck flask provided with a stirrer, a thermometer and a nitrogen gas-introducing tube, followed by cooling the suspension down to 0° C. with ice with stirring, dropwise adding a THF solution (30 ml) of 4-[trans-4-[(E,Z)-2-(trans-4-propylcyclohexyl)vinyl]cyclohexyl]-2,6-difluorobenzonitrile (11.5 g, 30.9 mmols) prepared at the step 1), for 40 minutes while keeping the temperature at 0 ° C., thereafter raising the temperature up to room temperature, stirring for 20 hours, as it was, pouring the reaction solution into a 10% aqueous solution of sodium thiosulfate (300 ml), separating the dichloromethane layer, further extracting the aqueous layer with dichloromethane (200 ml), mixing the extract layers, washing with a saturated aqueous solution of sodium carbonate (600 ml) and water (600 ml) in this order, drying over anhydrous magnesium sulfate and distilling off the solvent under reduced pressure, to obtain an oxirane derivative (white crystals) (9.80 g).

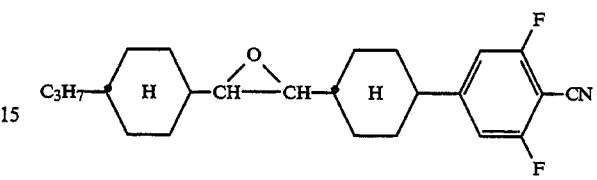

3) The oxirane derivative (9.80 g, 25.2 mmols) obtained at the step 2), dibromotriphenylphosfolan (17.0 g, 40.3 mmols) and toluene (300 ml) were fed into an eggplant type flask provided with a stirrer, a thermometer and a cooling tube, followed by heating the mixture under reflux for 6 hours, pouring the reaction solution into ice-cooled water, filtering off toluene-insolubles through Celite, adding fresh toluene (200 ml) for extracting, washing the extract layer with water (600 ml), a saturated aqueous solution of sodium carbonate (300 ml) and water (600 ml), in this order, drying over magnesium sulfate, and distilling off the solvent under reduced pressure, to obtain a reaction mixture (10.5 g). The reaction mixture was purified according to silica gel column chromatography using toluene as a developing solvent, followed by recrystallizing only erythro-form substance from toluene, to obtain a dibromoderivative (colorless crystals) (4.5 g).

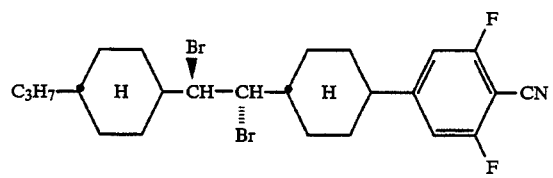

4) The dibromo-substance (3.8 g, 7.4 mmols) prepared at the step 3) was suspended in acetic acid (45 ml) in nitrogen gas atmosphere in an eggplant type flask provided with a stirrer, followed by adding zinc powder (3.6 g, 55.4 mmols), stirring the mixture at room temperature for 17 hours, filtering off insolubles from the reaction solution, extracting the reaction solution with ethyl acetate (200 ml), washing the extract layer with water (200 ml), a saturated aqueous solution of sodium carbonate (100 ml) and water (400 ml), in this order, drying over anhydrous magnesium sulfate, and distilling off the solvent under reduced pressure, to obtain a reaction product (2.9 g). The reaction product was purified according to silica gel column chromatography using heptane as a developing solvent, followed by recrystallizing from ethyl acetate, to obtain the finally objective substance, 4-[trans-4-[(E)-2-(trans-4-propylcyclohexyl)vinyl]cyclohexyl]-2,6-difluorobenzonitrile (colorless crystals) (1.6 g).

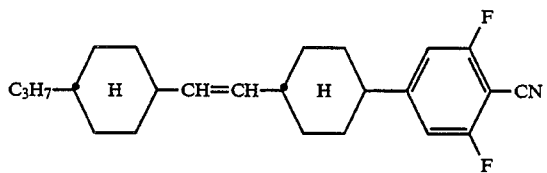

CN point: 75.1°–76.0° C.
NI point: 163.3°–163.5° C.
$^1$H-NMR ($\delta$ppm): 5.3–5.4 (2H, m, —CH=CH—)
6.8–7.0 (2H, m, aromatic proton)

In the same manner as that of the above preparation, by replacing 4-propylcyclohexylmethylbromide by 4-alkylcyclohexylmethylbromides having different alkyl groups, it is possible to prepare the following 4-[trans-4-[(E)-2-(trans-4-alkylcyclohexyl)vinyl]cyclohexyl]-2,6-difluorobenzonitriles:

4-[trans-4-[(E)-2-(trans-4-methylcyclohexyl)vinyl]cyclohexyl]-2,6-difluorobenzonitrile,
4-[trans-4-[(E)-2-(trans-4-ethylcyclohexyl)vinyl]cyclohexyl]-2,6-difluorobenzonitrile,
4-[trans-4-[(E)-2-(trans-4-butylcyclohexyl)vinyl]cyclohexyl]-2,6-difluorobenzonitrile,
4-[trans-4-[(E)-2-(trans-4-pentylcyclohexyl)vinyl]cyclohexyl]-2,6-difluorobenzonitrile,
4-[trans-4-[(E)-2-(trans-4-hexylcyclohexyl)vinyl]cyclohexyl]-2,6-difluorobenzonitrile,
4-[trans-4-[(E)-2-(trans-4-heptylcyclohexyl)vinyl]cyclohexyl]-2,6-difluorobenzonitrile,
4-[trans-4-[(E)-2-(trans-4-octylcyclohexyl)vinyl]cyclohexyl]-2,6-difluorobenzonitrile,
4-[trans-4-[(E)-2-(trans-4-nonylcyclohexyl)vinyl]cyclotlexyl]-2,6-difluorobenzonitrile,
4-[trans-4-[(E)-2-(trans-4-decylcyclohexyl)vinyl]cyclohexyl]-2,6-difluorobenzonitrile.

EXAMPLE 6 (Use example 1)

A nematic liquid crystal of a liquid crystal composition (A) consisting of

| | |
|---|---|
| 4-(4-propylcyclohexyl)benzonitrile | 30 wt. %, |
| 4-(4-pentylcyclohexyl)benzonitrile | 40 wt. % and |
| 4-(4-heptylcyclohexyl)benzonitrile | 30 wt. %, | has a clearing point (Cp) of 52.3° C.

An element obtained by filling this liquid crystal composition in a TN cell (twisted nematic cell) having a thickness of 9 μm exhibited an operation threshold voltage (V10) of 1.60 V, a dielectric anisotropy value ($\Delta\epsilon$) of +10.7, an optical anisotropy value (An) of 0.119 and a viscosity ($\eta_{20}$) of 21.7 cP. This liquid crystal composition (85 wt. %, as mother liquid crystal) was blended with 4-[trans-4-[(E)-2-(trans-4-ethylcyclohexyl)vinyl]cyclohexyl]-2-fluorobenzonitrile (15 wt. %) shown in Example 3, and the values of the physical properties were measured. The results were as follows:
Cp: 65.0° C., $\Delta\epsilon$: 11.5, An: 0.122,
$\eta_{20}$: 24.6 cP and V$_{10}$: 1.49.

Further, when the composition was allowed to stand in a freezer at −20° C. for 20 days, no deposit of crystal was observed.

EXAMPLE 7 (Use example 2)

The composition shown in Use example 1 (85 wt. %, as mother liquid crystal) was blended with 4-[trans-4-[(E)-2-(trans-4-propylcyclohexyl)vinyl]cyclohexyl]-2-fluorobenzonitrile (15 wt. %) shown in Example 4, and the values of the physical properties were measured. The results were as follows:
Cp: 68.8° C., Ae: 11.7, An: 0.123,
$\eta_{20}$: 25.0 cP and V$_{10}$: 1.57.

Further, when this composition was allowed to stand in a freezer at −20° C. for 20 days, no deposit of crystal was observed.

COMPARATIVE EXAMPLE

The CN points and NI points of compounds expressed by the above-described formula (ii), and the threshold voltages (V$_{10}$), dielectric anisotropy values ($\Delta\epsilon$) and viscosities of two liquid crystal compositions obtained by blending the respective compounds (each 15 wt. %) with the composition (A) (85 wt. %) are shown in Table 1 together with the results of Examples 6 and 7.

TABLE 1

| Compound | CN point | NI point | V$_{10}$ | $\Delta_\epsilon$ | $\eta_{20}$ |
|---|---|---|---|---|---|
| C$_2$H$_5$—[H]—CH=CH—[H]—⟨⟩—F (with F) | 35.9 | 95.2 | 2.03 | 8.0 | 34.4 |
| C$_3$H$_7$—[H]—CH=CH—[H]—⟨⟩—F (with F) | 39.2 | 132.8 | 1.82 | 6.0 | 22.4 |
| C$_2$H$_5$—[H]—CH=CH—[H]—⟨⟩—CN (with F) (Example 6) | 74.3 | 188.5 | 1.49 | 11.5 | 24.6 |

TABLE 1-continued

| Compound | CN point | NI point | $V_{10}$ | $\Delta_\epsilon$ | $\eta_{20}$ |
| --- | --- | --- | --- | --- | --- |
| 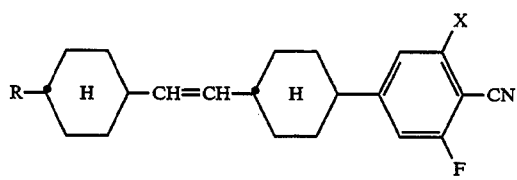 | 48.0 | 215.5 | 1.57 | 11.7 | 25.0 |
| (Example 7) | | | | | |

What we claim is:

1. A 2-fluorobenzonitrile derivative expressed by the formula $$R-\underset{H}{\bigcirc}-CH=CH-\underset{H}{\bigcirc}-\underset{F}{\bigcirc}^{X}-CN \quad (I)$$

wherein R represents a hydrogen atom or a linear or branched alkyl group of 1 to 10 carbon atoms, X represents a hydrogen atom or a fluorine atom, and the vinyl group has a transconfiguration.

2. A 4-[trans-4-[(E)-2-(trans-4-alkylcyclohexyl)vinyl]-cyclohexyl]-2-fluorobenzonitrile, expressed by the formula (I) according to claim 1, wherein said X represents a hydrogen atom.

3. A 4-[trans-4-[(E)-2-(trans-4-alkylcyclohexyl)vinyl]-cyclohexyl]-2,6-difluorobenzonitrile, expressed by the formula (I) according to claim 1, wherein said X represents a fluorine atom.

4. A liquid crystal composition comprising at least two components at least one of which is a compound as set forth in claim 1.

* * * * *